US010443363B2

(12) United States Patent
Canalizo-Hernandez et al.

(10) Patent No.: US 10,443,363 B2
(45) Date of Patent: Oct. 15, 2019

(54) METHOD AND SYSTEM FOR CORE FLOOD TESTING FOR RESERVOIR SOURING STUDIES

(71) Applicants: Monica A. Canalizo-Hernandez, Houston, TX (US); Dennis R. Enning, Spring, TX (US); Gary L. McDonald, Friendswood, TX (US)

(72) Inventors: Monica A. Canalizo-Hernandez, Houston, TX (US); Dennis R. Enning, Spring, TX (US); Gary L. McDonald, Friendswood, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 31 days.

(21) Appl. No.: 15/685,316

(22) Filed: Aug. 24, 2017

(65) Prior Publication Data
US 2018/0119531 A1    May 3, 2018

Related U.S. Application Data

(60) Provisional application No. 62/415,123, filed on Oct. 31, 2016.

(51) Int. Cl.
*E21B 43/20* (2006.01)
*E21B 43/24* (2006.01)
(Continued)

(52) U.S. Cl.
CPC .............. *E21B 43/20* (2013.01); *E21B 43/24* (2013.01); *G01N 33/241* (2013.01);
(Continued)

(58) Field of Classification Search
CPC ...... G01N 33/24; G01N 33/38; G01N 33/241; G01N 2203/0222; G01N 2203/023; E21B 43/20; E21B 43/24; E21B 41/0092
(Continued)

(56) References Cited

U.S. PATENT DOCUMENTS 4,253,327 A * 3/1981 Wiley ................ G01N 15/0826
73/38
4,753,107 A * 6/1988 Reed .................. G01N 15/0806
73/38
(Continued)

FOREIGN PATENT DOCUMENTS

WO    WO2009/009382    1/2009
WO    WO 2015/034845 A1    3/2015
WO    WO 2016/016677 A1    2/2016

OTHER PUBLICATIONS

Jones, C. et al., "The Use of Realistic Physiochemical Conditions to Demonstrate the Ability of Third Generation THPS to Control Reservoir Souring and MIC," Paper No. 4042, Corrosion 2014, San Antonio, TX (Mar. 9-13, 2014), pp. 1-14.
(Continued)

*Primary Examiner* — Octavia Hollington
(74) *Attorney, Agent, or Firm* — ExxonMobil Upstream Research Company-Law Department

(57) ABSTRACT

An apparatus and method for testing a core rock sample for reservoir souring. The apparatus includes first and second pumps, and a piston cell associated with each of the first and second pumps. Each piston cell has a first portion and a second portion divided by a movable piston such that the second portion is fluidly sealed from the first portion. Each piston cell is configured to receive fluid pumped by its respective pump into the first portion thereof. A core holder is sized to receive and maintain a core rock sample at a desired pressure and temperature. The second portions of each of the piston cells are fluidly connected to the core holder.

21 Claims, 2 Drawing Sheets

(51) Int. Cl.
*G01N 33/24* (2006.01)
*E21B 41/00* (2006.01)

(52) U.S. Cl.
CPC .... *E21B 41/0092* (2013.01); *G01N 2203/023* (2013.01); *G01N 2203/0222* (2013.01)

(58) Field of Classification Search
USPC .......................................................... 73/784
See application file for complete search history.

(56) References Cited

U.S. PATENT DOCUMENTS

| | | | |
|---|---|---|---|
| 4,856,967 A * | 8/1989 | Jones | ...................... F04B 9/105 |
| | | | 417/342 |
| 5,263,360 A * | 11/1993 | Blauch | .................... C09K 8/58 |
| | | | 166/250.02 |
| 5,493,226 A | 2/1996 | Honarpour et al. | |
| 8,252,576 B2 | 8/2012 | Campbell et al. | |
| 8,517,092 B2 | 8/2013 | Ward | |
| 8,573,300 B2 | 11/2013 | Alsop et al. | |
| 8,585,899 B2 | 11/2013 | Baldwin et al. | |
| 8,895,479 B2 | 11/2014 | Roldan Carrillo et al. | |
| 9,062,542 B2 | 6/2015 | Sahni et al. | |
| 9,804,062 B2 * | 10/2017 | Collins | ................... E21B 43/20 |
| 9,989,512 B2 * | 6/2018 | Haggerty | ................ E21B 49/00 |
| 2012/0241149 A1 | 9/2012 | Chen et al. | |
| 2014/0301984 A1 | 10/2014 | Corrin et al. | |

OTHER PUBLICATIONS

Maxwell, S. et al., "Laboratory Studies of Microbicide and Nitrate Strategies for MIC and Reservoir Souring Mitigation" Paper No. 08663, NACE International, Corrosion 2008 Conference & Expo, (2008), pp. 1-12.

Yin, B. et al., "A Study of Biofilm Growth and Control in Porous Media Bioreactors," Paper No. 4129, Corrosion 2014, San Antonio, TX (Mar. 9-13, 2014), pp. 1-11.

* cited by examiner

METHOD AND SYSTEM FOR CORE FLOOD TESTING FOR RESERVOIR SOURING STUDIES

CROSS-REFERENCE TO RELATED APPLICATION

This application claims the benefit of U.S. Provisional Patent Application Ser. No. 62/415,123, filed Oct. 31, 2016, entitled METHOD AND SYSTEM FOR CORE FLOOD TESTING FOR RESERVOIR SOURING STUDIES, the entirety of which is incorporated by reference herein.

BACKGROUND

Field of Disclosure

The disclosure relates generally to souring of a hydrocarbon reservoir, and more particularly, to methods of testing core rock samples to predict reservoir souring.

Description of Related Art

This section is intended to introduce various aspects of the art, which may be associated with the present disclosure. This discussion is intended to provide a framework to facilitate a better understanding of particular aspects of the present disclosure. Accordingly, it should be understood that this section should be read in this light, and not necessarily as an admission of prior art.

Reservoir Souring is a phenomenon associated with seawater injection in which levels of hydrogen sulfide ($H_2S$) increase over time in a previously sweet (no $H_2S$) hydrocarbon reservoir. The increase of $H_2S$ is a result of the growth of Sulfate Reducing Bacteria (SRB) or Sulfate Reducing Prokaryotes (SRP) within the reservoir. The effectiveness of the limited commercially available technologies proposed to mitigate reservoir souring is not consistent in the field. The factors that determine whether an approach is successful or not for a particular field are not well understood. A critical limitation for the understanding and evaluation of mitigation technologies is the lack of a laboratory testing capability that closely simulates all the key reservoir conditions. Currently, laboratory evaluations that are performed using devices at either ambient pressures or reservoir pressures do not incorporate reservoir rock or mimic the transport of the fluids and bacterial growth in biofilm form within the reservoir rock pores.

The publication "Laboratory Studies of Microbicide and Nitrate Strategies for MIC and Reservoir Souring Mitigation", NACE 2008, paper 08663, reported the use of columns filled with glass beads to simulate the reservoir rock porous space and grow biofilm under continuous flow. This device, used to evaluate biocide and nitrate as souring mitigation technologies, did not incorporate the high pressure and temperature of the reservoir, the hydrocarbon phase, or rock mineralogy. Use of similar columns has also been proposed in Yin, et al., "A Study of Biofilm Growth and Control in Porous Media Bioreactors" Corrosion 2014, Paper 4129. Additionally, Jones, et al. "The Use of Realistic Physiochemical Conditions to Demonstrate the Ability of Third Generation THPS to Control Reservoir Souring and MIC" Corrosion 2014, paper 4042, used pressurized heated columns packed with sand to simulate reservoir conditions to grow bacteria and evaluate biocides. These sand columns do not account for key reservoir rock properties, including permeability, porosity, wettability, connectivity and mineralogy. What is needed is a laboratory capability that simulates reservoir souring by growing bacteria under simulated reservoir conditions to advance the understanding of reservoir souring and to evaluate potential mitigation technologies under conditions that simulate reservoir conditions and that are relevant to actual fields.

SUMMARY

The present disclosure provides an apparatus for testing a core rock sample. The apparatus includes a first pump. A first piston cell has a movable piston dividing the first piston cell into a first portion and a second portion that is fluidly sealed from the first portion. The first piston cell is configured to receive fluid pumped by the first pump into the first portion thereof. The apparatus also includes a second pump. A second piston cell has a movable piston dividing the second piston cell into a first portion and a second portion that is fluidly sealed from the first portion. The second piston cell is configured to receive fluid pumped by the second pump into the first portion thereof. A core holder is sized to receive and maintain a core rock sample at a desired pressure and temperature. The second portion of the first piston cell and the second portion of the second piston cell are fluidly connected to the core holder.

The present disclosure also provides methods of testing a core rock sample. According to some such methods, a first fluid is pumped into a first compartment of a first piston cell to move a piston and thereby place pressure on a second fluid in a second compartment of the first piston cell. A third fluid is pumped into a first compartment of a second piston cell to move a piston and thereby place pressure on a fourth fluid in a second compartment of the second piston cell. The second fluid is injected, under pressure from the first piston cell, into a core holder containing the core rock sample. The fourth fluid is injected, under pressure from the second piston cell, into the core holder. For a predetermined time, a pressure and temperature are maintained in the core holder similar to a pressure and temperature at a location from which the core rock sample was taken. After the predetermined time, the second fluid is injected into the core holder to thereby cause effluent to exit the core holder through an outlet. The effluent is tested for the presence of hydrogen sulfide. The second fluid is injected into the core holder until steady levels of hydrogen sulfide are detected if hydrogen sulfide is present in the effluent. The pressure and the temperature are maintained for an additional time if hydrogen sulfide is not present in the effluent.

The present disclosure provides further methods of testing a core rock sample. For instance, in each of a first plurality of piston cells, a first fluid is pumped into a first compartment to move a piston therein and thereby place pressure on anoxic seawater in a second compartment. In each of a second plurality of piston cells, the first fluid is pumped into a first compartment to move a piston and thereby place pressure on a fluid comprising at least one of bacteria or a reservoir souring mitigation treatment in a second compartment. The anoxic seawater is injected, under pressure from the first plurality of piston cells, into a core holder containing the core rock sample. The fluid comprising at least one of bacteria or a reservoir souring mitigation treatment is injected, under pressure from the second plurality of piston cells, into the core holder. For a predetermined time, a pressure and temperature are maintained in the core holder similar to a pressure and temperature at a location from which the core rock sample was taken. After the predetermined time, anoxic seawater is injected into the core holder to thereby cause effluent to exit the core holder through an outlet. The effluent is tested for the presence of hydrogen sulfide. If hydrogen sulfide is present in the effluent, the anoxic seawater is injected into the core holder until steady levels of hydrogen sulfide are detected. The pressure and the temperature are maintained for an additional time if hydrogen sulfide is not present in the effluent.

The foregoing has broadly outlined the features of the present disclosure so that the detailed description that follows may be better understood. Additional features will also be described herein.

BRIEF DESCRIPTION OF THE DRAWINGS

These and other features, aspects and advantages of the disclosure will become apparent from the following description, appending claims and the accompanying drawings, which are briefly described below.

Figure 1:
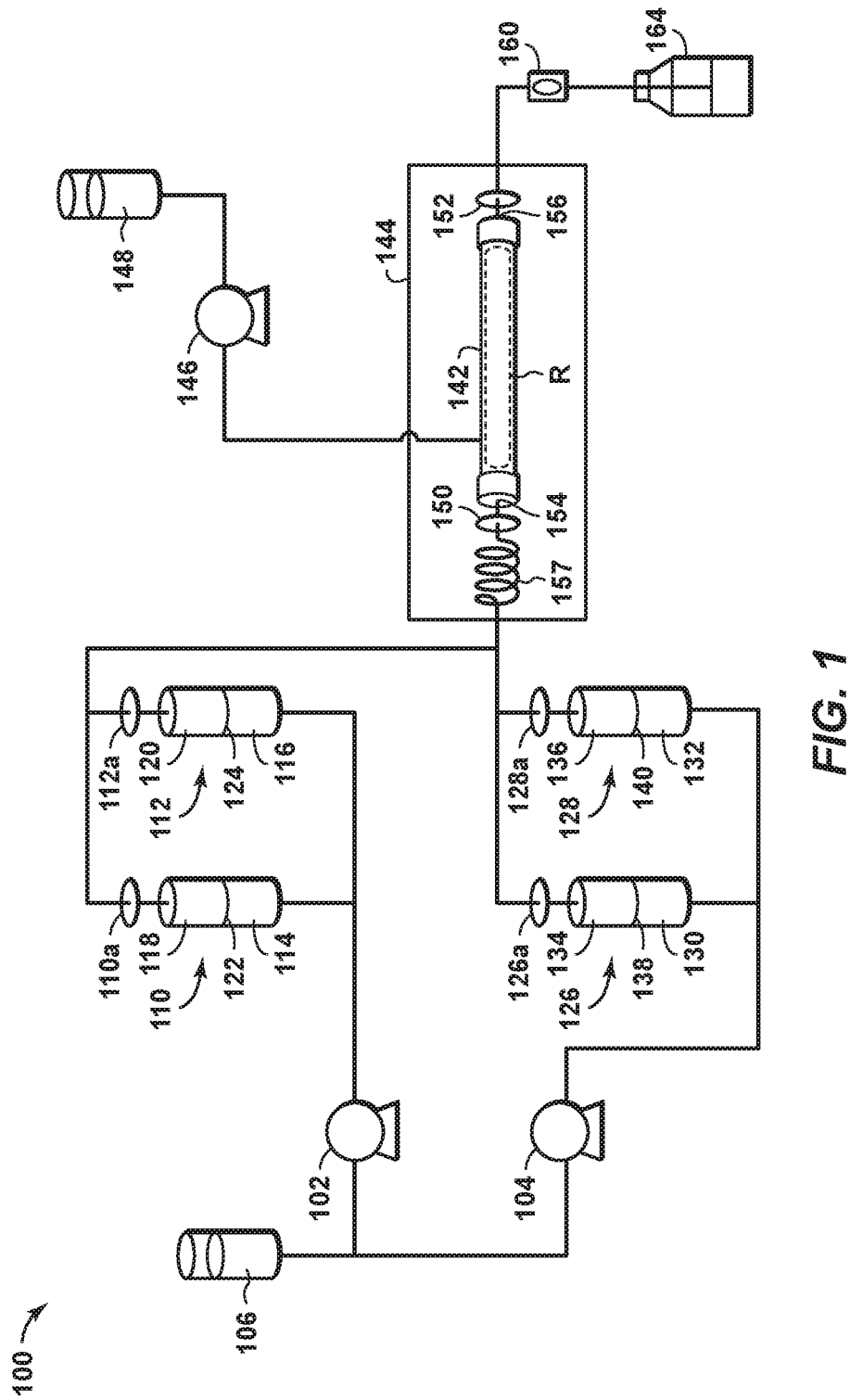
FIG. 1 is a schematic diagram of a system for core flood testing for reservoir souring studies according to disclosed aspects.

It should be noted that the figures are merely examples and no limitations on the scope of the present disclosure are intended thereby. Further, the figures are generally not drawn to scale, but are drafted for purposes of convenience and clarity in illustrating various aspects of the disclosure.

DETAILED DESCRIPTION

To promote an understanding of the principles of the disclosure, reference will now be made to the features illustrated in the drawings and specific language will be no limitation of the scope of the disclosure is thereby intended. Any alterations and further modifications, and any further applications of the principles of the disclosure as described herein are contemplated as would normally occur to one skilled in the art to which the disclosure relates. For the sake of clarity, some features not relevant to the present disclosure may not be shown in the drawings.

At the outset, for ease of reference, certain terms used in this application and their meanings as used in this context are set forth. To the extent a term used herein is not defined below, it should be given the broadest definition persons in the pertinent art have given that term as reflected in at least one printed publication or issued patent. Further, the present techniques are not limited by the usage of the terms shown below, as all equivalents, synonyms, new developments, and terms or techniques that serve the same or a similar purpose are considered to be within the scope of the present claims.

As one of ordinary skill would appreciate, different persons may refer to the same feature or component by different names. This document does not intend to distinguish between components or features that differ in name only. The figures are not necessarily to scale. Certain features and components herein may be shown exaggerated in scale or in schematic form and some details of conventional elements may not be shown in the interest of clarity and conciseness. When referring to the figures described herein, the same reference numerals may be referenced in multiple figures for the sake of simplicity. In the following description and in the claims, the terms "including" and "comprising" are used in an open-ended fashion, and thus, should be interpreted to mean "including, but not limited to."

The articles "the," "a" and "an" are not necessarily limited to mean only one, but rather are inclusive and open ended so as to include, optionally, multiple such elements.

As used herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numeral ranges provided. Accordingly, these terms should be interpreted as indicating that insubstantial or inconsequential modifications or alterations of the subject matter described and are considered to be within the scope of the disclosure.

Aspects described herein provide a high-pressure and high-temperature core flooding capability (bio-core) test system and method that incorporates all the key reservoir parameters and simulates reservoir souring. Core rock plug from a specific reservoir is saturated with field produced fluids (oil and formation water) at reservoir pressure and temperature, and field seawater used for injection is continuously injected into the rock. Using this capability, steady levels of $H_2S$ that are representative of the field are produced after bacterial growth has been established within the rock under these conditions. Mitigation technologies can then be evaluated for their effect on $H_2S$ levels and on rock properties under simulated reservoir conditions. In addition, key parameters which govern reservoir souring, and the efficacy of various souring mitigation methods, can be measured and incorporated into reservoir souring modeling tools. This methodology is superior to other capabilities as it includes all the reservoir conditions in the testing, providing information on the performance of proposed mitigation technologies under these extreme conditions, and on the effect of mitigation technologies and souring on reservoir properties (e.g. permeability).

FIG. 1 shows a system 100 for core flood testing of a core rock R for reservoir souring studies according to disclosed aspects. System 100 includes first and second pumps 102, 104. First and second pumps 102, 104 may be pneumatic pumps, and in one aspect may be selected to reach flow rates that simulate field injection rates and/or field production rates. For example, first and second pumps may be selected to reach flow rates of up to 10 ml/minute. A distilled water source 106 provides an input to each of the first and second pumps 102, 104. The first and second pumps 102, 104 pump distilled water from the distilled water source 106 into a bottom compartment or portion of one or more piston cells. In the aspect shown in FIG. 1, the one or more piston cells associated with the first pump 102 include a first piston cell 110 and a second piston cell 112. Each of the first and second piston cells 110, 112 has a bottom compartment or portion 114, 116 in fluid communication with the first pump 102, and a top compartment or portion 118, 120 configured to be filled with sterile anoxic seawater. A piston 122, 124 separates the top and bottom portions of the first and second piston cells 110, 112 such that the top and bottom portions of each of the first and second piston cells are not in fluid communication with each other. Also included in the aspect shown in FIG. 1 are third and fourth piston cells 126, 128. Similar to the first and second piston cells, each of the third and fourth piston cells 126, 128 has a bottom portion 130, 132 in fluid communication with the second pump 104 and a top portion 134, 136 configured to be filled with bacteria or a reservoir souring mitigation treatment. A piston 138, 140 separates the top and bottom portions of the third and fourth piston cells 126, 128 such that the top and bottom portions of each of the third and fourth piston cells are not in fluid communication with each other.

A core holder 142 in fluid communication with the top portions 118, 120, 134, 136 of each of the first, second, third, and fourth piston cells 110, 112, 126, 128. The core holder 142 is sized to be able to accept a core rock sample R. The core holder 142 may be enclosed in a temperature-controlled environment, which in FIG. 1 is shown as an oven 144, which may be a convection oven, capable of maintaining temperatures similar to what may be experienced at the location the core rock sample R was taken. For example, the oven 144 may be capable of maintaining temperatures of between 30° C. and 200° C. An overburden pump 146 may be used to apply a containment pressure, or an overburden pressure, to a source of distilled water 148 or, alternatively, a gas. The overburden pump 146 may be a peristaltic or pneumatic pump. The distilled water 148 is in fluid communication with the core holder containing the core rock sample that has been previously wrapped to avoid direct contact with the liquid, and thus the containment pressure, or the overburden pressure, is applied to the core rock sample inside the core holder 142. In an aspect, the containment or overburden pressure applied to the core rock sample may be at least 2000 psia, but in any event the containment or overburden pressure applied to the core rock sample should be greater than the back pressure applied at the outlet of the core. The back pressure regulator may be a dome back pressure regulator. The back pressure is set to mimic the reservoir pressure. Differential pressure sensors 150, 152 may be installed at the inlet 154 and the outlet 156 of the core holder 142, respectively, to monitor changes in the core rock sample during any experiments or processes. An extended length of tubing 157 may be disposed in the oven 144. The extended length of tubing 157 is in fluid communication with the top portions 118, 120, 134, 136 of each of the first, second, third, and fourth piston cells 110, 112, 126, 128 at one end thereof and the core holder 142 at the other end thereof. The extended length of tubing 157 has a length sufficient to ensure fluids entering the core holder are at the oven temperature and the core rock sample R prior to entering the core holder 142. In an aspect, the length of the extended length of tubing 157 may be as long as twenty feet (6.1 m).

A sampling port 160 may be installed outside the oven 144, and preferably downstream of the outlet 156 of the core holder 142 at a location that minimizes the distance between the outlet and the sampling port 160. In this manner, fluid retention in tubing downstream of the core is thereby minimized. In an aspect, this distance may be less than 1 ft (30 cm). The sampling port 160 may be a small glass chamber that retains a small liquid volume (1-5 mL) with rubber septum with a crimp cover to enable the sample to be extracted without oxygen contamination. The sampling port 160 allows for collection and analysis of the effluent exiting the core holder to determine amounts of $H_2S$, organic acid and other nutrients, bacteria population, bacteria numbers, and/or any other desired characteristic of the effluent. A waste collector 164 may be located downstream of the sampling port 160. The waste collector 164 may contain a high concentration sodium hydroxide solution to neutralize any $H_2S$ present in the effluent.

In an aspect, system 100 may be used in the following manner. A core rock sample, if not preserved, may be cleaned of native fluids following routine protocols. If the core rock sample contains oil, cleaning is preferred, followed by saturation with formation water, which may be a field sample or a synthetic formulation. If the core rock sample contains native formation water, cleaning is not performed. Saturation of the core rock sample with field hydrocarbon for 10 pore volumes or higher is then performed. Next, field fluids are injected into the core at a flow rate of between 0.1 mL/minute and 10 mL/minute. The injected fluids may be field-produced water, a mixture of produced water and injection water, or produced water that has been treated to increase SRB numbers and to have a bacteria population actively producing hydrogen sulfide. This injection operation is preferably performed by first and second pumps 102, 104, which pump distilled water 106 into the lower half 114, 116, 130, and 132 of first through fourth piston cells 110, 112, 126, 128 at a flow rate of up to 10 mL/minute. Each piston 122, 124, 138, 140 is thereby pushed upward, thereby pushing the field fluids in the top half 118, 120, 134, 136 of the first through fourth piston cells into the core rock sample R disposed in the core holder 142. As previously discussed, this fluid may include sterile anoxic seawater, souring mitigation treatment, bacteria, or the like. Such use of the piston cells allows for the fluid injected in the core rock sample to remain sterile and free of oxygen throughout the experiment, and minimizes the equipment contact with the injected fluid. Sterile (bacteria free) and oxygen free fluids (anoxic) are required to induce SRB growth within the core rock sample and avoid growth of other competing organisms within the piston cell compartments 110, 112, 126 and 128. Using two pumps allows for simultaneous injections of various fluids, such as seawater and mitigation treatments. Filters 110a, 112a, 126a, 128a may be installed in the outlet of each piston cell 110, 112, 126, 128 to prevent injection of any undesired particles or organisms. As previously described, between 1-10 pore volumes of field fluid is injected into the core rock sample R to ensure saturation. The core rock sample is shut in under pressure and is maintained within the oven 144 at the test temperature for a saturation time, which may be between 2-10 weeks.

At the conclusion of the saturation time, seawater from the first and second piston cells 110, 112 is caused to flow into the core holder 142. The liquid in core holder 142 flows out of the core holder as effluent, and a portion of the effluent is removed using the sampling port 160 to be tested for the presence of hydrogen sulfide. If hydrogen sulfide is not detected in the effluent, then the core rock sample R is "shut in" inside the core holder 142 for an additional period of time at a desired temperature and pressure, and additional field fluids may be injected into the core holder 142 prior to being shut in, if necessary. On the other hand, if hydrogen sulfide is detected in the effluent, then the seawater is directed to flow through the core rock sample R until steady levels of hydrogen sulfide are detected. At that point, a desired reservoir souring mitigation technology may be injected into the core rock sample R to test its efficacy. Injection of the mitigation solution may be continuous or periodic.

Figure 2:
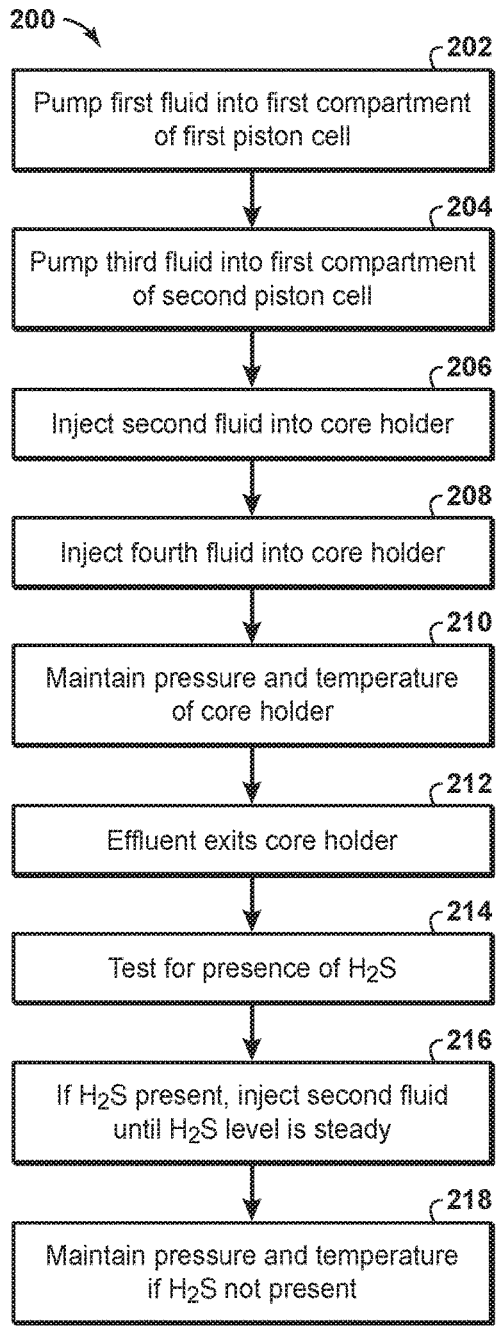
FIG. 2 is a method according to aspects of the present disclosure.

FIG. 2 is a flowchart of a method 200 for testing a core rock sample according to disclosed aspects. At block 202 a first fluid, which may be distilled water, is pumped into a first compartment of a first piston cell to move a piston and thereby place pressure on a second fluid in a second compartment of the first piston cell. At block 204 a third fluid, which may be the same as the first fluid, is pumped into a first compartment of a second piston cell to move a piston and thereby place pressure on a fourth fluid in a second compartment of the second piston cell. At block 206 the second fluid, under pressure from the first piston cell, is injected into a core holder containing the core rock sample. At block 208 the fourth fluid, under pressure from the second piston cell, is injected into the core holder. At block 210, for a predetermined time a pressure and temperature are maintained in the core holder similar to a pressure and temperature at a location from which the core rock sample was taken. At block 212, after the predetermined time, the second fluid is injected into the core holder, to thereby cause effluent to exit the core holder through an outlet. At block 214 the effluent is tested for the presence of hydrogen sulfide. At block 216, if hydrogen sulfide is present in the effluent, the second fluid is injected into the core holder until steady levels of hydrogen sulfide are detected. At block 218 the pressure and the temperature are maintained for an additional time if hydrogen sulfide is not present in the effluent, and the second fluid may also be injected into the core holder.

Figure 3:
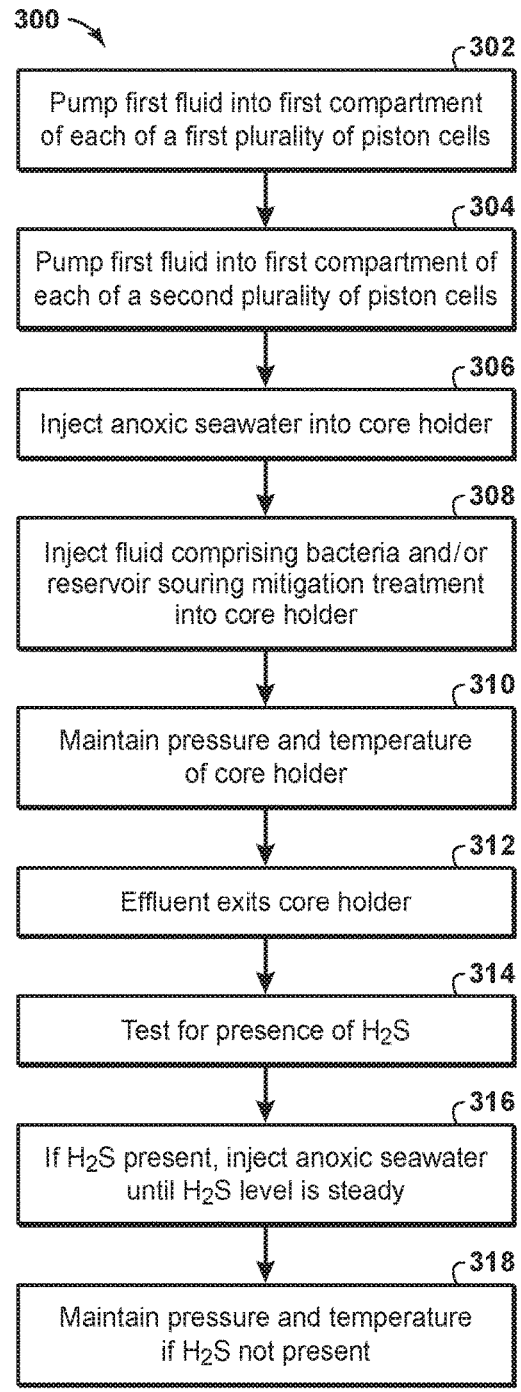
FIG. 3 is a method according to other aspects of the present disclosure.

FIG. 3 is a flowchart of a method 300 for a method of testing a core rock sample according to disclosed aspects. At block 302, in each of a first plurality of piston cells, a first fluid is pumped into a first compartment to move a piston therein and thereby place pressure on anoxic seawater in a second compartment. At block 304, in each of a second plurality of piston cells, the first fluid is pumped into a first compartment to move a piston and thereby place pressure on a fluid comprising at least one of bacteria or a reservoir souring mitigation treatment in a second compartment. At block 306 the anoxic seawater, which is under pressure from the first plurality of piston cells, is injected into a core holder containing the core rock sample. At block 308 the fluid comprising at least one of bacteria or a reservoir souring mitigation treatment, under pressure from the second plurality of piston cells, is injected into the core holder. At block 310, for a predetermined time, a pressure and temperature are maintained in the core holder similar to a pressure and temperature at a location from which the core rock sample was taken. At block 312, anoxic seawater is injected into the core holder after the predetermined time, to thereby cause effluent to exit the core holder through an outlet. At block 314 the effluent is tested for the presence of hydrogen sulfide. At block 316, if hydrogen sulfide is present in the effluent, the anoxic seawater is injected into the core holder until steady levels of hydrogen sulfide are detected. At block 318, the pressure and the temperature are maintained for an additional time if hydrogen sulfide is not present in the effluent, and the anoxic seawater may also be injected into the core holder.

It is believed that the disclosure set forth herein encompasses multiple distinct inventions with independent utility. The specific embodiments disclosed and illustrated herein are not to be considered in a limiting sense as numerous variations are possible.

Illustrative, non-exclusive example of systems and methods according to the present disclosure have been presented. While the present disclosure may be susceptible to various modifications and alternative forms, the exemplary embodiments discussed herein have been shown only by way of example. However, it should again be understood that the present disclosure is not intended to be limited to the particular embodiments disclosed herein. Indeed, the present disclosure includes all alternatives, modifications, and equivalents falling within the true spirit and scope of the appended claims.

What is claimed is:

1. An apparatus for testing a core rock sample, comprising:
   a first pump;
   a first piston cell having a movable piston dividing the first piston cell into a first portion and a second portion that is fluidly sealed from the first portion, the first piston cell configured to receive fluid pumped by the first pump into the first portion thereof;
   a second pump;
   a second piston cell having a movable piston dividing the second piston cell into a first portion and a second portion that is fluidly sealed from the first portion, the second piston cell configured to receive fluid pumped by the second pump into the first portion thereof;
   a core holder sized to receive and maintain a core rock sample at a desired pressure and temperature, wherein the second portion of the first piston cell and the second portion of the second piston cell are fluidly connected to the core holder; and
   a filter disposed between the second portion of the first or second piston cells and the core holder.

2. The apparatus of claim 1, wherein the fluid pumped by at least one of the first pump and second pump is water.

3. The apparatus of claim 1, wherein the second portion of the first piston cell contains anoxic seawater.

4. The apparatus of claim 1, wherein the second portion of the second piston cell contains bacteria or a reservoir souring mitigation treatment.

5. The apparatus of claim 1, further comprising an overburden pump fluidly connected to the core holder and configured to apply a containment pressure to the core rock sample.

6. The apparatus of claim 1, further comprising an oven in which the core holder is disposed, the oven configured to maintain the core rock sample at the desired temperature.

7. The apparatus of claim 6, further comprising an extended length of tubing disposed inside the oven and fluidly connected at a first end to the second portions of the first and second piston cells and fluidly connected at a second end to the core holder.

8. The apparatus of claim 1, further comprising a sampling port at an outlet of the core holder, the sampling port configured to permit collection and analysis of effluent exiting the core holder.

9. The apparatus of claim 1, further comprising:
   a third piston cell having a movable piston dividing the third piston cell into a first portion and a second portion that is fluidly sealed from the first portion, the third piston cell configured to receive fluid pumped by the first pump into the first portion of the third piston cell; and
   a fourth piston cell having a movable piston dividing the fourth piston cell into a first portion and a second portion that is fluidly sealed from the first portion, the fourth piston cell configured to receive fluid pumped by the second pump into the first portion of the fourth piston cell;
   wherein the second portion of the third piston cell and the second portion of the fourth piston cell are fluidly connected to the core holder; and
   wherein the second portion of the third piston cell contains anoxic seawater, and the second portion of the fourth piston cell contains bacteria or a reservoir souring mitigation treatment.

10. A method of testing a core rock sample, comprising:
    pumping a first fluid into a first compartment of a first piston cell to move a piston and thereby place pressure on a second fluid in a second compartment of the first piston cell;

pumping a third fluid into a first compartment of a second piston cell to move a piston and thereby place pressure on a fourth fluid in a second compartment of the second piston cell;

injecting the second fluid, under pressure from the first piston cell, into a core holder containing the core rock sample;

injecting the fourth fluid, under pressure from the second piston cell, into the core holder;

for a predetermined time, maintaining a pressure and temperature in the core holder similar to a pressure and temperature at a location from which the core rock sample was taken;

after the predetermined time, injecting the second fluid into the core holder, to thereby cause effluent to exit the core holder through an outlet;

testing the effluent for the presence of hydrogen sulfide;

if hydrogen sulfide is present in the effluent, injecting the second fluid into the core holder until steady levels of hydrogen sulfide are detected; and maintaining the pressure and the temperature for an additional time if hydrogen sulfide is not present in the effluent.

11. The method of claim 10, further comprising:
situating the core holder in an oven to maintain the temperature in the core holder similar to the temperature at the location from which the core rock sample was taken.

12. The method of claim 10, further comprising:
sampling effluent exiting an outlet of the core holder for at least one of organic acids, hydrogen sulfide, bacteria population, and bacteria numbers.

13. The method of claim 10, wherein the second fluid and the fourth fluid are injected into the core holder until the core rock sample is saturated with a combination of the second fluid and the fourth fluid.

14. The method of claim 10, wherein the first fluid and the third fluid comprises distilled water.

15. The method of claim 10, wherein the second fluid comprises anoxic seawater.

16. The method of claim 10, wherein the fourth fluid comprises bacteria or a reservoir souring mitigation treatment.

17. The method of claim 10, further comprising using an overburden pump to maintain the pressure in the core holder for the predetermined time.

18. The method of claim 10, further comprising sampling the effluent within 30 centimeters of the outlet of the core holder.

19. The method of claim 10, further comprising injecting the second fluid into the core holder if hydrogen sulfide is not present in the effluent.

20. A method of testing a core rock sample, comprising:
in each of a first plurality of piston cells, pumping a first fluid into a first compartment to move a piston therein and thereby place pressure on anoxic seawater in a second compartment;

in each of a second plurality of piston cells, pumping the first fluid into a first compartment to move a piston and thereby place pressure on a fluid comprising at least one of bacteria or a reservoir souring mitigation treatment in a second compartment;

injecting the anoxic seawater, under pressure from the first plurality of piston cells, into a core holder containing the core rock sample;

injecting the fluid comprising at least one of bacteria or a reservoir souring mitigation treatment, under pressure from the second plurality of piston cells, into the core holder;

for a predetermined time, maintaining a pressure and temperature in the core holder similar to a pressure and temperature at a location from which the core rock sample was taken;

after the predetermined time, injecting anoxic seawater into the core holder, to thereby cause effluent to exit the core holder through an outlet;

testing the effluent for the presence of hydrogen sulfide;

if hydrogen sulfide is present in the effluent, injecting the anoxic seawater into the core holder until steady levels of hydrogen sulfide are detected; and maintaining the pressure and the temperature for an additional time if hydrogen sulfide is not present in the effluent.

21. The method of claim 20, further comprising injecting the anoxic seawater if hydrogen sulfide is not present in the effluent.

* * * * *